US006607702B1

United States Patent
Kang et al.

(12) United States Patent
(10) Patent No.: US 6,607,702 B1
(45) Date of Patent: Aug. 19, 2003

(54) PHOTOCATALYST FILTER, METHOD FOR FABRICATING THE SAME AND AIR CLEANER THEREOF

(75) Inventors: Kwang Ok Kang, Kyongsangnam-do (KR); Young Ki Hong, Kyongsangnam-do (KR); Kyong Wook Heo, Kyongsangnam-do (KR); Sung Hwa Lee, Kyongsangnam-do (KR); Soo Yeon Shin, Kyongsangnam-do (KR); Jung Hun Kang, Kyongsangnam-do (KR); Yong Bok Choi, Kyongsangnam-do (KR); Ju Han Yoon, Kyongsangnam-do (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 09/362,552

(22) Filed: Jul. 28, 1999

(30) Foreign Application Priority Data

May 27, 1999 (KR) .................................. 99-19269

(51) Int. Cl.[7] .......................... B01J 35/02; B01D 53/86
(52) U.S. Cl. ...................... 422/186.3; 422/4; 422/5; 422/121; 422/122; 422/24
(58) Field of Search ................. 422/121, 4, 5, 422/122, 186.3, 22, 24; 55/486, 524; 428/312.8

(56) References Cited

U.S. PATENT DOCUMENTS 5,853,866 A * 12/1998 Watanabe et al. ......... 428/312.8
5,948,355 A * 9/1999 Fujishima et al. ............. 422/4
6,149,717 A * 11/2000 Satyapal et al. ............... 96/16
6,191,062 B1 * 2/2001 Hayakawa et al. ......... 502/159

FOREIGN PATENT DOCUMENTS

| JP | 09308809 A * | 5/1996 |
| JP | 1013538 | 5/1998 |
| JP | 2000-197827 | 7/2000 |
| WO | WO 9812048 A1 * | 3/1998 |

* cited by examiner

Primary Examiner—Robert J. Warden, Sr.
Assistant Examiner—Sean E. Conley
(74) Attorney, Agent, or Firm—Fleshner & Kim, LLP

(57) ABSTRACT

Photocatalyst filter, method for fabricating the same, and air cleaner thereof, the photocatalyst filter including a base material of a required shape, an enamel layer consisting of frit for forming an inorganic layer and additives for forming a porous surface layer as main composition coated on a surface of the base material, and a photocatalyst layer consisting of a photocatalyst solution consisting of a photocatalyst and a dispersion solvent and bonding agents as main composition coated on the enamel layer, and the method including the steps of (1) coating an enamel layer on a surface of a base material subjected to pretreatment for removal of foreign matters, the enamel layer consisting of frit for forming an inorganic layer on a surface of the base material and additives for forming a porous surface layer on the surface of the base material as main composition, and (2) coating a photocatalyst layer on the enamel layer; the photocatalyst layer consisting of a photocatalyst solution and bonding agents as main composition, the photocatalyst solution consisting of a photocatalyst and a dispersion solvent.

23 Claims, 9 Drawing Sheets

FIG.3A enamel thickness of coated layer:61~109 μm

FIG.3B enamel+TiO₂ thickness of coated layer:60~110 μm

FIG.3C enamel+TiO$_2$(+Zeolite 10%)

thickness of coated layer:60~110 μm

FIG.3D enamel(+Zeolite 10%)+TiO$_2$ thickness of coated layer:48~98 μm

PHOTOCATALYST FILTER, METHOD FOR FABRICATING THE SAME AND AIR CLEANER THEREOF

BACKGROUND OF THE INVENTION

1. Field of the Invention

The present invention relates to a photocatalyst filter, a method for fabricating the same, and an air cleaner thereof, and more particularly, to a photocatalyst filter, a method for fabricating the same, and an air cleaner thereof which is suitable for application to various home appliances, such as an air conditioner.

2. Background of the Related Art

In general, different air cleaners are used in homes and industrial sites. For example, the air cleaners are used in waste incineration plants and stacks of factories for removing harmful substances of dusts contained in exhaust gases. The air cleaners are also used in homes for maintaining clean environments, and various filters are mounted on air conditioners, fan heaters, vacuum cleaners, and the like for cleaning the air. Conventionally, for air cleaning, either non-woven fabric of, in general, polypropylene(PP) resin fiber or polyethylene(PE) resin fiber, or electrostatic precipitator type filters are used. However, though the foregoing types of filters can filtrate dusts, removal of odor or sterilization of microbes are difficult in view of the system. Therefore, separate deodorization filters of activated carbon is used for deodorization. However, the deodorization filter of activated carbon has problems in that a deodorization performance is poor and a lifetime is short, and harmful microbes can not be sterilized.

To solve those problems, there have been researches and developments for so called photocatalyst technologies using photocatalyst which is activated by photo-energy to provide sterilizing and deodoring functions, of which typical one is titanium oxide $TiO_2$. Photocatalysts, such as titanium oxide have strong adsorptive powers, and, moreover, form different radicals upon excited on exposure to a photo-energy, to provide a strong oxidizing power, enough to sterilize microbes and to react with, and decompose substances which cause odor.

Figure 1:
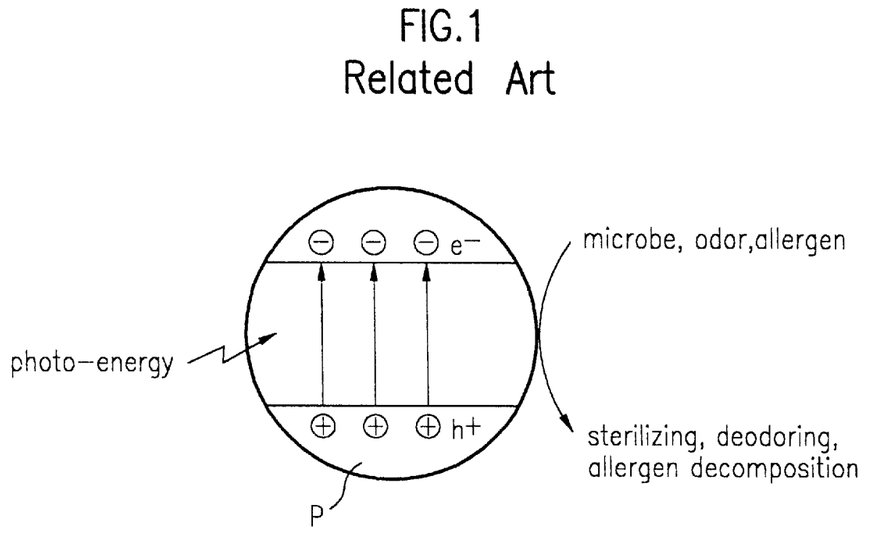
FIG. 1 illustrates a reaction diagram showing a reaction mechanism of the photocatalyst, schematically.

A mechanism of the photocatalyst reaction will be explained with reference to FIG. 1.

When a photo-energy of over a certain strength emitted form an UV lamp is directed onto a photo-catalyst P, an electron in a valence band is transited to a conduction band, to produce an electron $e^-$ and a hole $h^+$. The electron and hole, having a strong oxidizing power and a strong reducing power respectively, makes reaction with water vapor $H_2O$ and oxygen $O_2$ in air, to form active oxygens, such as OH radical, H radical, super oxide anion $O_2^-$, which have strong coupling force with other to break a coupling of odoring substance, thereby making deodoring. That is, an OH radical breaks coupling of an organic substance which causes odor, and makes a direct coupling with the organic substance, leaving water vapor and carbon dioxide, that allows to remove the odor. And, OH radical having a strong oxidizing power sterilizes microbes. That is, as an allergen or a microbe has a protein with amino acid polypeptide coupled thereto as a main component, OH radical breaks the polypeptide coupling of the amino acid, to alter the protein, thereby decomposing the allergen and sterilize the microbe. And, the electron or the hole makes a direct coupling to an organic substance to break a coupling of the organic substance, which eventually leaves water vapor and carbon dioxide, that allows deodoring. Thus, sterilization, deodorization and allergen decomposition can be achieved using photocatalyst.

Despite of the aforementioned excellent performances of the photocatalyst, a range of application of photocatalyst to air cleaning is extremely restricted in the related art since use of filters of photocatalyst in air cleaners or domestic air conditioners is very difficult. Because the photocatalyst is required to be coated on a frame of a desired shape for use the photocatalyst in the air conditioner and the like, which coating of the photocatalyst without fallen off of the coating is very difficult in the related art. This is because titanium oxide, a photocatalyst, having a poor affinity with inorganic material, such as metal or glass, is liable to fall off if coated on a base of such a material, and coating of the photocatalyst on an organic base causes decomposition of the organic material. In the related art, it was difficult to coat the photocatalyst on a base, i.e., on a metal plate or mesh, which acts as a frame of a filter. If the photocatalyst is used in an air conditioner or air cleaner provided with a suction fan, the photocatalyst is flown, that makes use of the photocatalyst in domestic appliances. Consequently, in most of cases in the related art, despite of the aforementioned excellent performances of the photocatalyst, the photocatalyst has been used in restricted fields, such as waste incineration plants by scattering the photocatalyst.

SUMMARY OF THE INVENTION

Accordingly, the present invention is directed to a photocatalyst filter, a method for fabricating the same, and an air cleaner thereof that substantially obviates one or more of the problems due to limitations and disadvantages of the related art.

An object of the present invention is to provide a photocatalyst filter suitable for use in domestic appliances as the photocatalyst is coated strongly on a base, a method for fabricating the same, and an air cleaner thereof.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the photocatalyst filter includes a base material of a required shape, an enamel layer consisting of frit for forming an inorganic layer and additives for forming a porous surface layer as main composition coated on a surface of the base material, and a photocatalyst layer consisting of a photocatalyst solution consisting of a photocatalyst and a dispersion solvent and bonding agents as main composition coated on the enamel layer.

In other aspect of the present invention, there is provided a method for fabricating a photocatalyst filter including the steps of (1) coating an enamel layer on a surface of a base material subjected to pretreatment for removal of foreign matters, the enamel layer consisting of frit for forming an inorganic layer on a surface of the base material and additives for forming a porous surface layer on the surface of the base material as main composition, and (2) coating a photocatalyst layer on the enamel layer; the photocatalyst layer consisting of a photocatalyst solution and bonding agents as main composition, the photocatalyst solution consisting of a photocatalyst and a dispersion solvent.

The photocatalyst layer further includes zeolite or copper ion exchanged zeolite, and the photocatalyst is preferably titanium oxide.

In another aspect of the present invention, there is provided an electrostatic precipitator having an ionizer and a collector, including the photocatalyst filter mounted in an air passage of the electrostatic precipitator.

In further aspect of the present invention, there is provided an air conditioner having a body with a suction grill and a discharge grill and an air filter mounted on the suction grill, including the photocatalyst filter mounted either on the suction grill or the discharge grill.

Thus, as the present invention facilitates a firm coating of the photocatalyst on a base material, use of the photocatalyst in various domestic appliances are allowed.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENT

Figure 2:
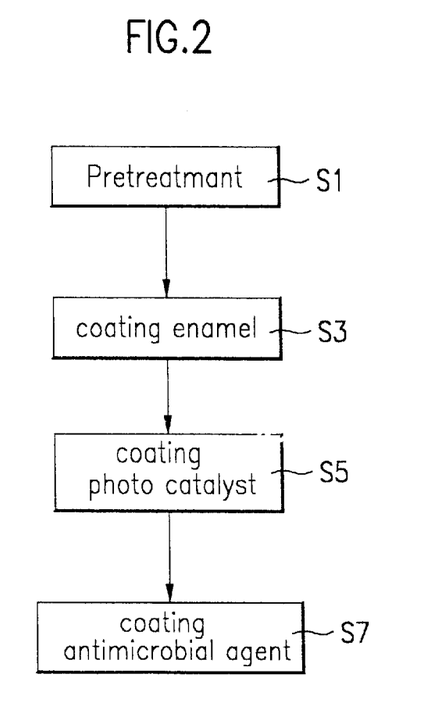
FIG. 2 illustrates steps of a method for fabricating a photocatalyst filter in accordance with a preferred embodiment of the present invention.

Reference will now be made in detail to the preferred embodiments of the present invention, examples of which are illustrated in the accompanying drawings. FIG. 2 illustrates steps of a method for fabricating a photocatalyst filter in accordance with a preferred embodiment of the present invention, and FIGS. 3A~3D illustrate ×100 SEM(Scanning Electron Microscope) photographs each showing an enlarged surface of different embodiments of the photocatalyst filter of the present invention.

First, foreign matters, such as oil on a base, a frame of a filter body, on which the photocatalyst to be coated, are removed(S1). Then, enamel is coated on the base material (S3). And, the photocatalyst is coated on a surface having enamel coated thereon(S5). In this instance, in order to strengthen an antimicrobial performance, a sterilizing agent or antimicrobial agent may be coated on the surface having the photocatalyst coated thereon, additionally(S7).

The steps of the method for fabricating a photocatalyst filter in accordance with a preferred embodiment of the present invention will be explained in detail.

It is preferable that the base material is formed of a metal taking a lifetime of the photocatalyst filter into consideration, more preferably, of aluminum because aluminum is a good material for coating enamel thereon. Of course, the base material may be in a variety of forms, such as, plate, or mesh, considering an apparatus on which the photocatalyst filter is to be mounted or a mounting position of the photocatalyst in the apparatus.

Composition of the enamel layer coated on the base material will be explained.

Figure 3A:
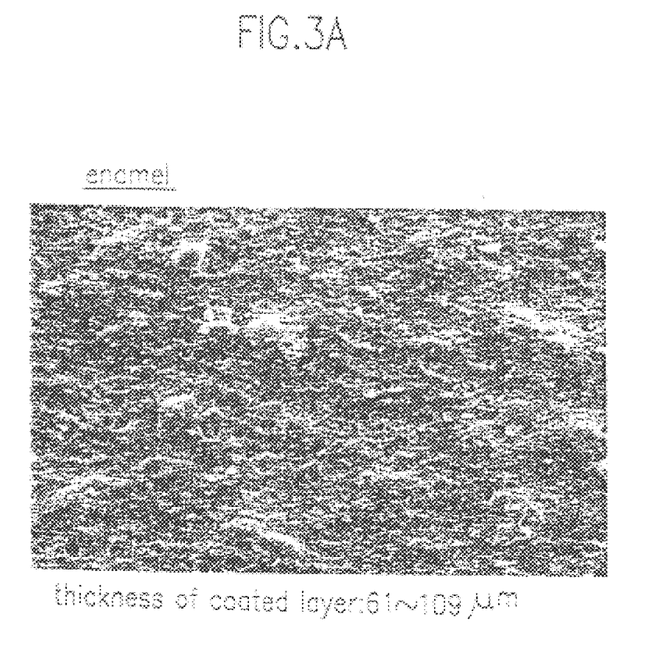
FIGS. 3A~3D illustrate photographs each showing an enlarged surface of different embodiments of the photocatalyst filter of the present invention.
Figure 4:
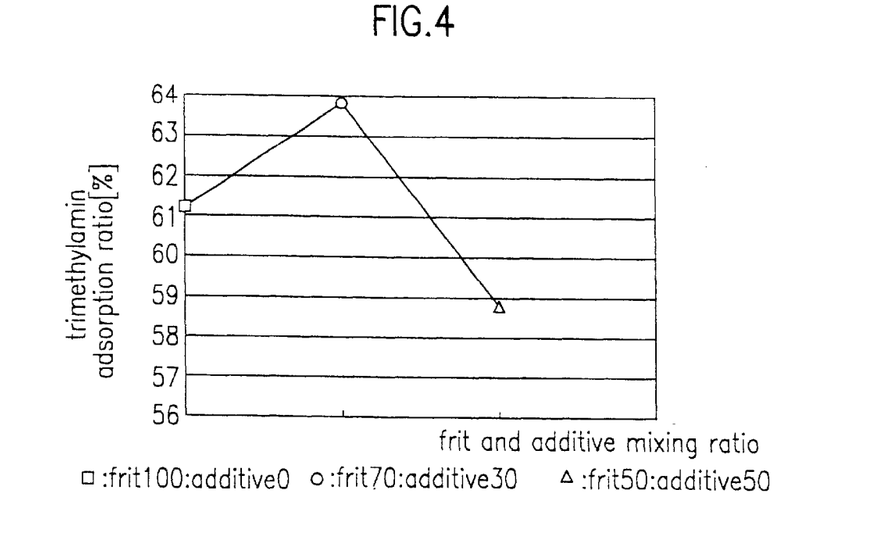
FIG. 4 illustrates a graph showing a deodoring efficiency vs. a mixing ratio of an enamel layer of a photocatalyst filter in accordance with a first preferred embodiment of the present invention.

An enamel solution to be sprayed onto the base material consists of a raw material of glass, i.e., vitreous frit, various additives and hardeners. The frit, mainly consisting of $SiO_2$, forms an inorganic surface layer to act as an undercoat, and the additives, acting to form a porous surface layer, mainly consist of oxides and alkali metals, such as $Al_2O_3$ and $TiO_2$(Rutile), Li, Na, Ca, and the like. And, in general, the additives are inclusive of set-up agents for stabilizing the additives, such as boric acid, $Na_2NO_2$, and the like and a suspension consisting of $SiO_2$—$Al_2O_3$—$H_2O$ for dispersing the additives. In the meantime, a mixing ratio of the frit and the additives is preferably 50:50~80:20 wt %, and, more preferably, 65:35~75:25 wt %. Because, as shown in FIG. 3A, an enamel layer with the above mixing ratio has a porosity to allow good infiltration of the photocatalyst coated thereon, that makes good coating. FIG. 4 illustrates a graph showing a deodoring efficiency vs. a mixing ratio of an enamel layer of frit and additives of a photocatalyst filter in accordance with a first preferred embodiment of the present invention, wherein an adsorption efficiency is calculated from measurements of residual concentration of trimethylamin after 20 minutes since addition of 20 ppm trimethylamin. As can be known from the graph, the deodoring efficiency is the best when the mixing ratio of the frit and the additives is 70:30. The enamel solution mixed thus is sprayed onto the base material, then, subjected to heat treatment at a temperature ranging 400~600° C. for approx. one hour, and, more preferably, at 550° C. for 20 min, and cooled down at a room temperature. FIG. 3A illustrates a photograph showing an enlarged surface of the enamel coating on the base material, wherefrom it can be known that the surface is porous.

Next, the steps of a process for coating the photocatalyst on the enamel layer will be explained, in detail.

The photocatalyst layer consists of a photocatalyst solution having a photocatalyst and a dispersion solvent and a bonding agent. In detail, the photocatalyst solution consists of TiO2 powder of anatase state as a main composition, mixed with dispersion solvents of isopropylalcohol, methanol, water and the like. The titanium oxide powder preferably has a mixing ratio of 10~30 wt % to the dispersion solvent. The bonding agent has $SiO_2$ as a main composition and is used for improving a coating quality and a lifetime of the titanium oxide coating. The a mixing ratio of the photocatalyst solution and the bonding agent is preferably 10:90~40:60 wt %, and more preferably 20:80~30:70 wt %. Too much use of the bonding agent deteriorates a photocatalyst performance of the titanium oxide, and too little use of the bonding agent deteriorates a bonding power. Then, the photocatalyst solution and the bonding agent are sprayed onto the enamel layer, and subjected to heat treatment at a temperature ranging 100~350° C. for less than approx. one hour, and preferably, at 200° C. for 30 minutes, and cooled down at a room temperature, for preventing deterioration of the titanium oxide while a lifetime of the titanium oxide is prolonged to the maximum, thereby completing fabrication of the photocatalyst filter.

Figure 5:
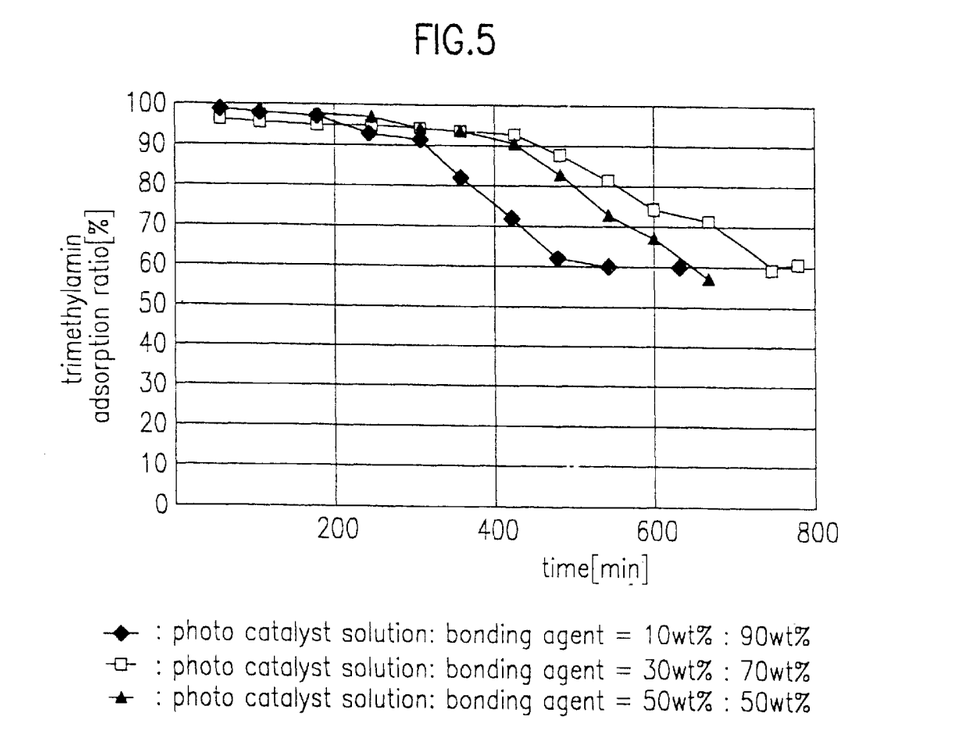
FIG. 5 illustrates a graph showing a deodoring efficiency vs. a mixing ratio of a photocatalyst solution and a bonding agent of a photocatalyst filter in accordance with a first preferred embodiment of the present invention.

FIG. 5 illustrates a graph showing a deodoring efficiency vs. a mixing ratio of a photocatalyst solution and a bonding agent of a photocatalyst filter in accordance with a first preferred embodiment of the present invention.

For the measurement, the photocatalyst filter in place in a 6 liter chamber, 160 ppm of trimethylamin, which is an odor gas, is injected thereto, and a residual concentration of the trimethylamin is measured at 60 min. intervals, from which measurement results the deodoring efficiency is calculated. As can be known from FIG. 5 that the deodoring efficiency is varied with the mixing ratio of the photocatalyst solution and the bonding agent, of which the mixing ratio of 30:70 wt % of the photocatalyst solution and the bonding agent exhibits a comparatively even deodoring efficiency.

Figure 3B:
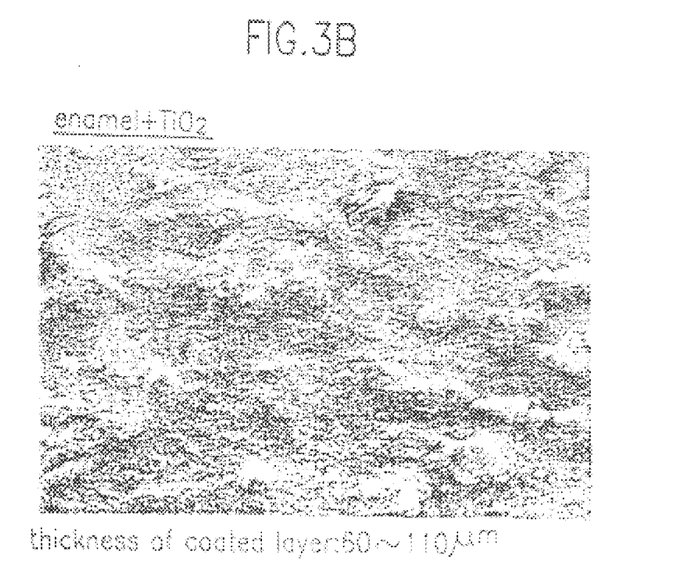
Figure 3C:
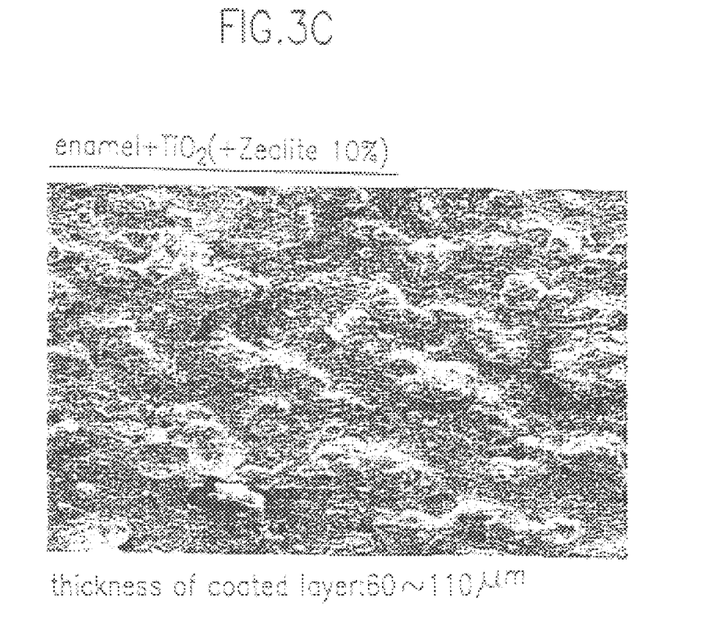

Another embodiment of the photocatalyst filter of the present invention will be explained. The steps of a process for fabricating a photocatalyst filter of this embodiment is identical to the first embodiment, except that a mixture of titanium oxide and zeolite is used as a main composition of the photocatalyst solution in this embodiment in place of the titanium oxide used in the first embodiment as a main composition of the photocatalyst solution. Though a photocatalyst solution coating of titanium oxide as a main composition on the enamel layer provides a smooth surface with a less porosity as shown in FIG. 3B, with a small surface area, a photocatalyst solution coating of a mixture of titanium oxide and zeolite as a main composition on the enamel layer provides a rugged surface with greater porosity as shown in FIG. 3C, with a large surface area, that improves the deodoring performance. Moreover, the photocatalyst mixed with, not the zeolite, but zeolite including metal ions, for example, copper ion exchanged zeolite is more preferable, because the copper has a sterilizing function. The copper ion exchanged zeolite Cu—A may be prepared by impregnating a zeolite powder in a $CuCl_2$ water solution, to exchange Na ions in the zeolite with Cu(II) ions, drying in air, and baking at 200° C. for three hours in an $H_2$ ambient. A preferable composition of the photocatalyst with a mix of the aforementioned zeolite or the copper ion exchanged zeolite is as follows. The mixture of titanium oxide and zeolite(or copper ion exchanged zeolite) preferably has a ratio of 10~30 wt % to the dispersion solvent. And, a mixing ratio of photocatalyst(a mixture of titanium oxide powder, zeolite or copper ion exchanged zeolite, and the dispersion solvent) and the bonding agent is preferably 10:90 wt %, and more preferably 20:80~30:70 wt %.

Though, in the aforementioned embodiments, zeolite is mixed with titanium oxide, and then coated on the enamel layer, zeolite may be mixed with enamel in advance, and then coated on the base material. However, in this case, a surface is obtained, which is smoother than the case when zeolite is mixed with titanium oxide, that drops a photocatalyst efficiency. Or photocatalyst and activated carbon may be mixed for coating on the surface of the enamel layer, because activated carbon costs lower than titanium oxide. In the photocatalyst coating, a secondary raw material such as a antimicrobial or sterilizing agent may be mixed with photocatalyst before coating, or the antimicrobial or sterilizing agent may be coated after the photocatalyst is coated. The antimicrobial or sterilizing agent is preferably one of Ag and Cu. By doing so, a photocatalyst filter with a prolonged lifetime, and even with deodoring and sterilizing functions can be obtained.

Figure 3D:
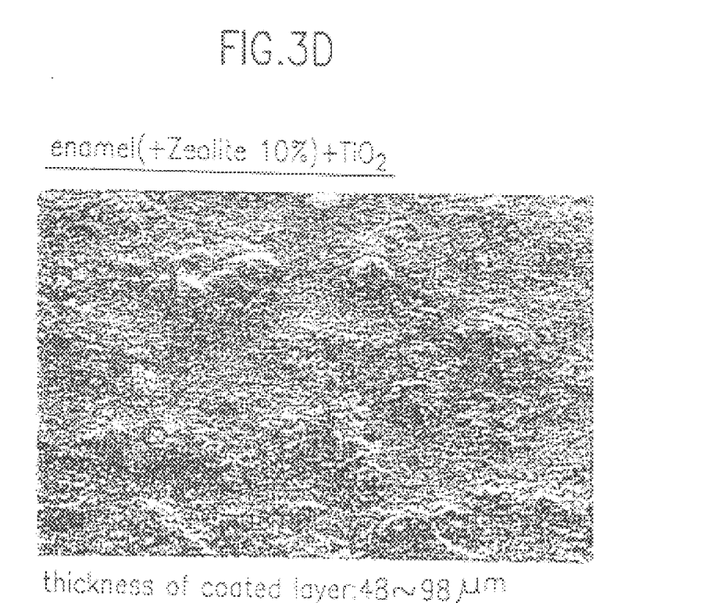
Figure 6:
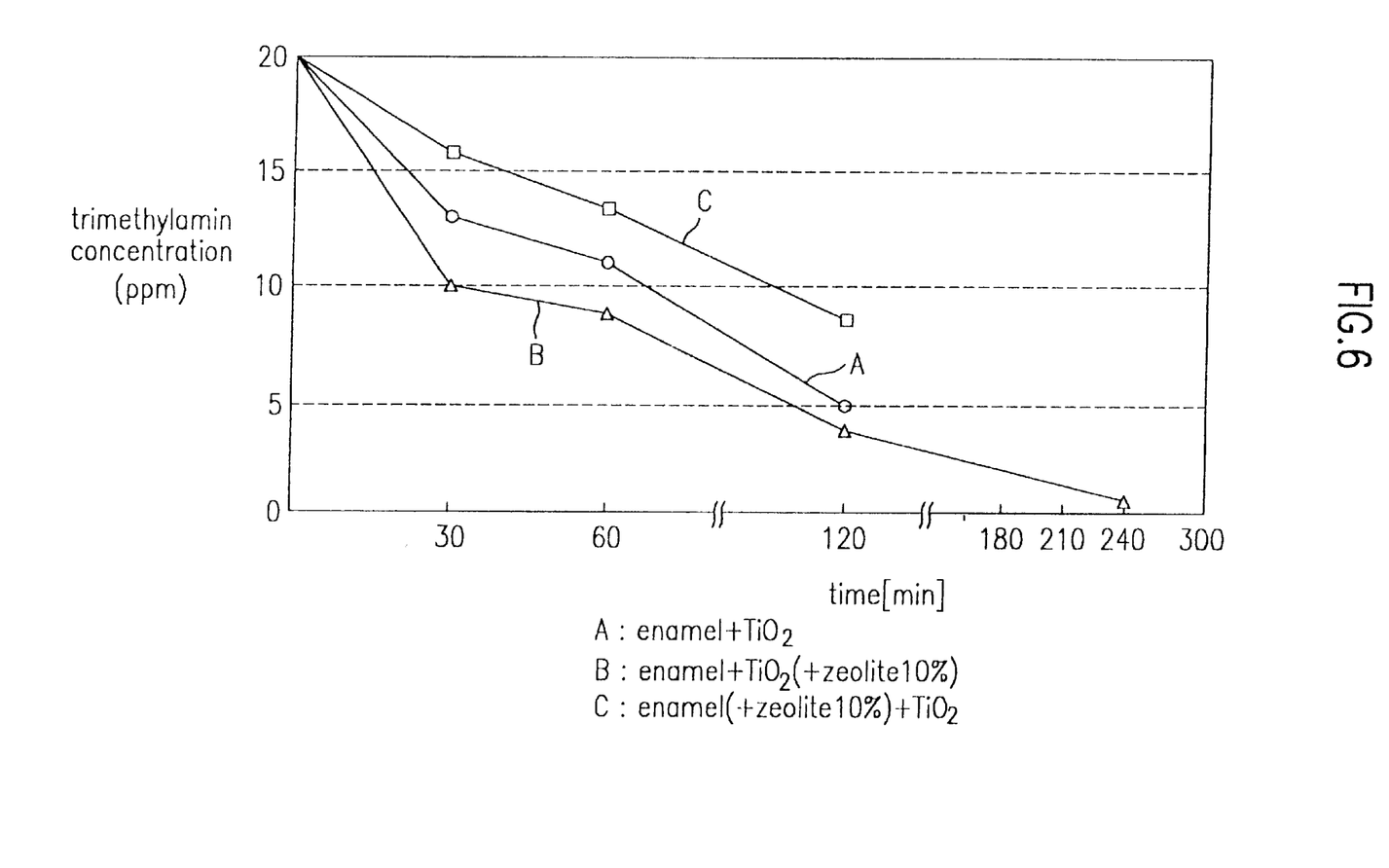
FIG. 6 illustrates a graph showing a deodoring efficiency of a photocatalyst filter in accordance with different preferred embodiments of the present invention.

FIG. 6 illustrates a graph showing a deodoring efficiency of a photocatalyst filter in accordance with different preferred embodiments of the present invention, obtained by measuring a residual concentration of trimethylamin at 30 minute intervals, 20 ppm of which is injected initially. 'A' denotes a photocatalyst filter having titanium oxide coated on the enamel layer (called as 'A' type photocatalyst filter), 'B' denotes a photocatalyst filter having a coating of a mixture of titanium oxide and zeolite(called as 'B' type photocatalyst filter), and 'C' denotes a photocatalyst filter having a coating of titanium oxide on a mixture of enamel and zeolite(called as 'C' type photocatalyst filter). As can be known from FIG. 6, an adsorption ratio of trimethylamin becomes better in an order of 'C' type, 'A' type, and 'B' type photocatalyst filters. This is because, as shown in FIGS. 3B~3D, a surface of the photocatalyst filter of 'B' type is the largest.

Figure 7:
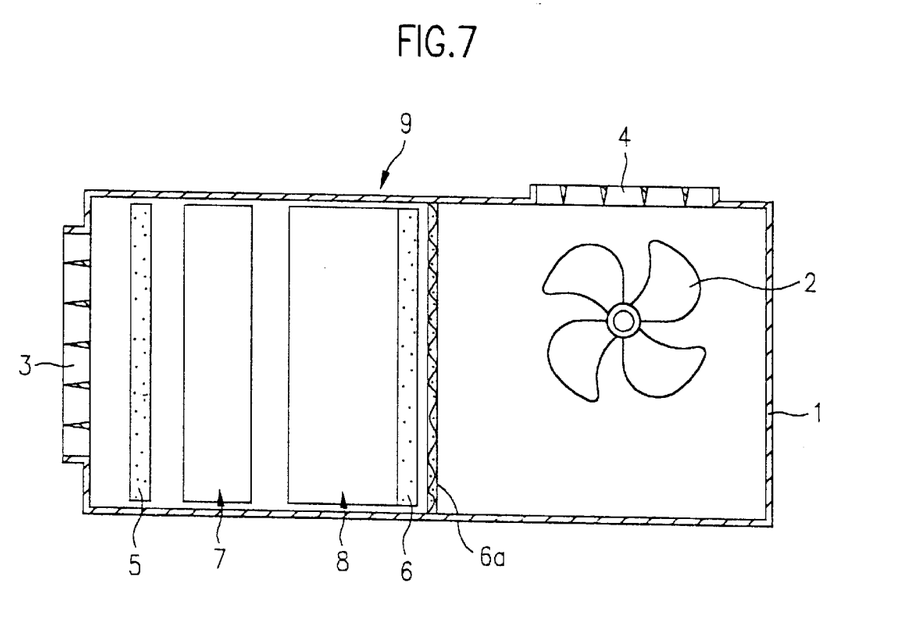
FIG. 7 illustrates an electrostatic precipitator having the photocatalyst filter of the present invention applied thereto, schematically.
Figure 8:
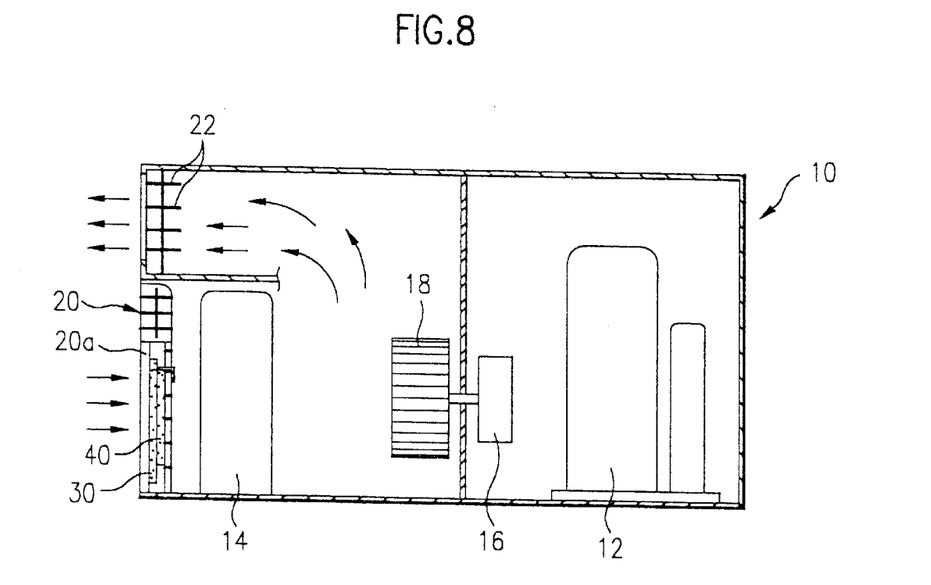
FIG. 8 illustrates an air conditioner having the photocatalyst filter of the present invention applied thereto, schematically.

Applications of the photocatalyst filter of the present invention will be explained with reference to FIGS. 7 and 8.

An electrostatic precipitator having the photocatalyst filter of the present invention applied thereto will be explained with reference to FIG. 7.

A general electrostatic precipitator 9 is provided with a body 1 having a suction grill 3 and a discharge grill 4, and a fan mounted in the body 1 for generating a suction power. And, there is an electrostatic precipitating unit in the body 1 having an ionizer 7 and a collector 8. There is prefilter 5 in front of the ionizer 7 for primary filtering of dusts in drawn air, and there is a deodoring filter 6 in rear of the collector 8 for removing odor component in air. In general, the deodoring filter 6 is formed of activated carbon.

The operation of the electrostatic precipitator 9 will be explained. Upon driving the fan 2, external air containing dusts and the like is drawn through the suction grill 3, and is involved in primary filtration of dusts therein at the prefilter 5. Then, the air is involved in charge of the dusts therein as the air passes through the ionizer 7 and collected at the collector 8. The air passes through the electrostatic precipitator is finally passes through the deodoring filter 6, and discharged to outside of the electrostatic precipitator through the discharge grill 4. However, the deodoring filter 6 of activated carbon has a poor deodoring performance, and has no sterilizing nor allergen decomposing power. And, a prolonged use of the deodoring filter 6 degrades the deodoring performance. However, mounting of the photocatalyst filer of the present invention in a position of a flow passage in the electrostatic precipitator 9 can improve the deodoring efficiency. In this instance, a mesh form of the photocatalyst filter 6a of the present invention may be mounted, or, without a separate mounting of the photocatalyst filter, the photocatalyst may be coated on one of components of the electrostatic precipitator, for example, on the ionizer 7, directly according to a method for fabricating a photocatalyst filter of the present invention.

An air conditioner having the photocatalyst filter of the present invention applied thereto will be explained with reference to FIG. 8.

Figure 9A:
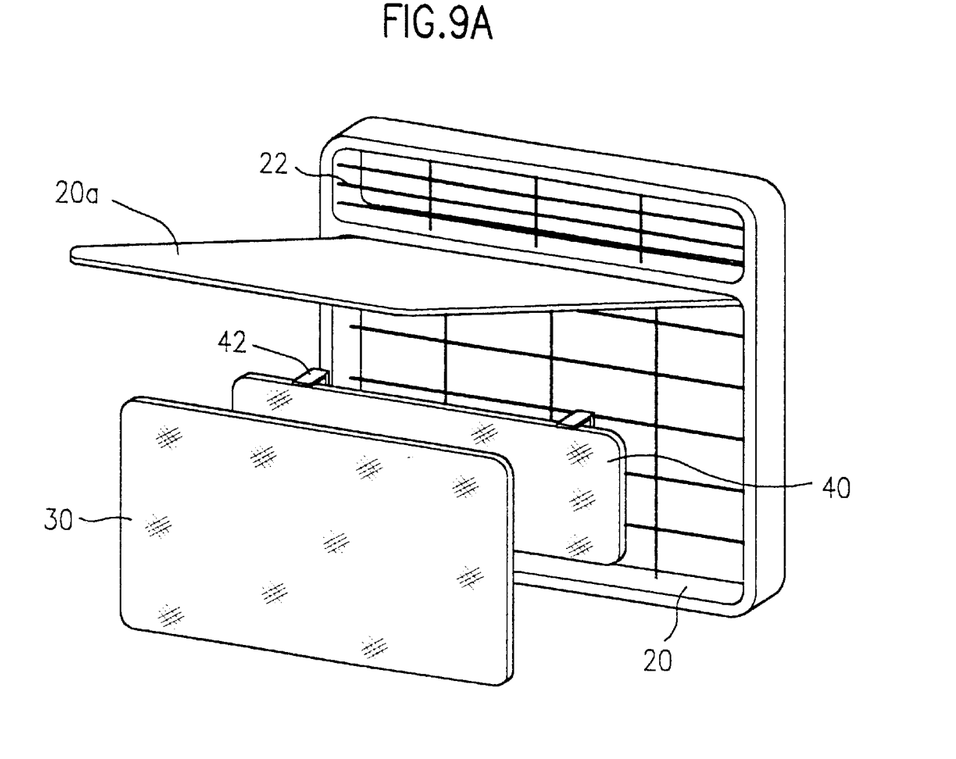
FIGS. 9A and 9B illustrate a disassembled perspective view and a section each showing a state of a mounted photocatalyst filter in FIG. 8.
Figure 9B:
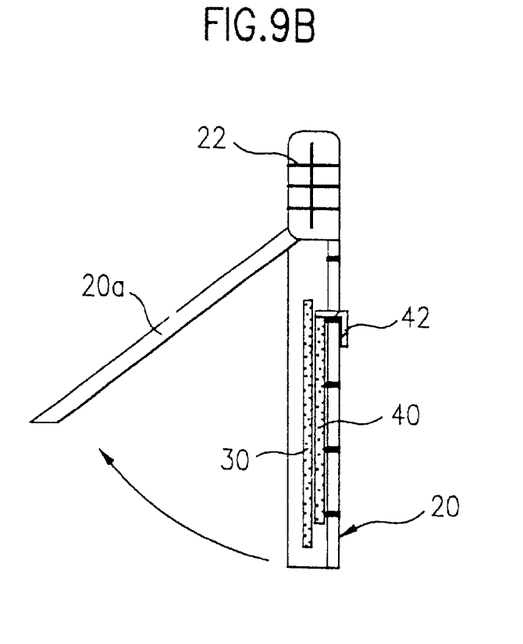
Figure 10:
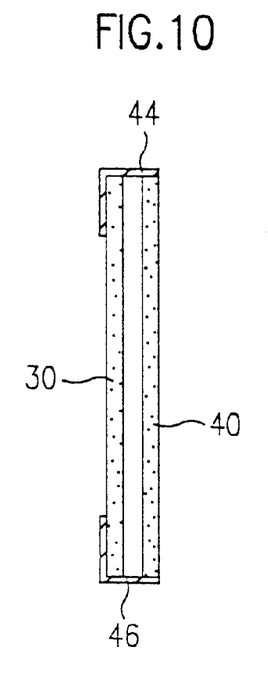
FIG. 10 illustrates a section showing a state of a mounted photocatalyst filter in FIG. 8 in accordance with another embodiment of mounting; and, FIGS. 11A~11C illustrate some of variations of the photocatalyst filter of the present invention.

A general air conditioner 10 is provided with a body having a suction grill 20 and a discharge grill 22, and a fan 18 with a motor 16 in the body for generating a suction power. And, there are a heat exchanger 14, a compressor 12, a condenser(not shown) and the like in the body, to form a refrigerating cycle. A suction grill cover 20a is rotatably fitted on the suction grill 20, and there is an air filter 30 mounted between the suction grill 20 and the suction grill cover 20a. In general, the air filter 30 of non-woven fabric or net only has a function to filtrate dusts in air. However, once the photocatalyst filter 40 of the present invention is mounted on the suction grill 20, the air conditioner 10 can be provided with a deodoring function. As shown in FIGS. 9A and 9B, the photocatalyst filter 40 may be provided with a hook 42 at a top thereof for mounting the photocatalyst filter 40 on the suction grill 20. And, as shown in FIG. 10, the photocatalyst filter 40 may be provided with hooks 44 and 46 at a top and a bottom thereof respectively for mounting the photocatalyst filter 40 on the related art suction filter 30 as a unit.

Figure 11A:
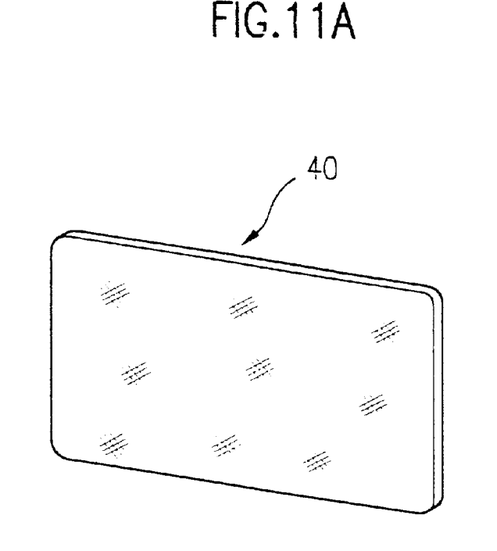
Figure 11B:
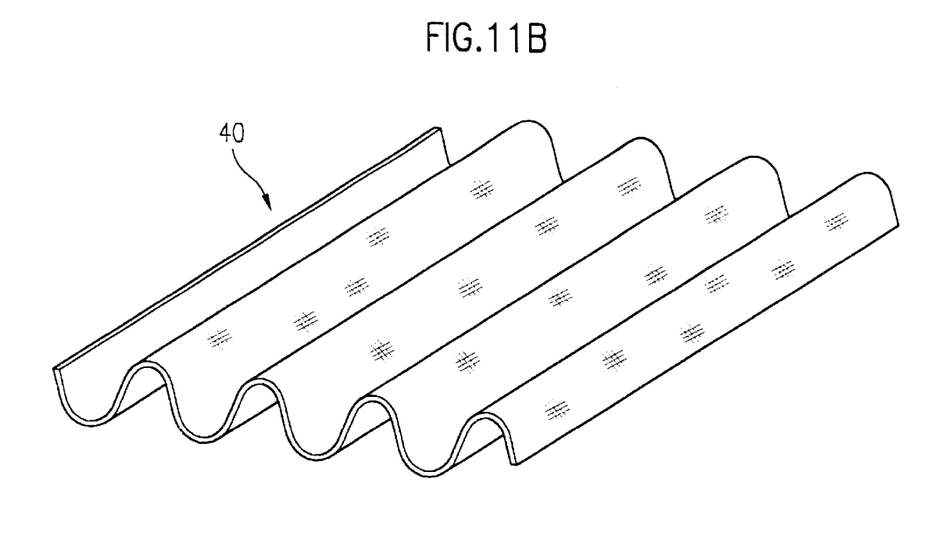
Figure 11C:
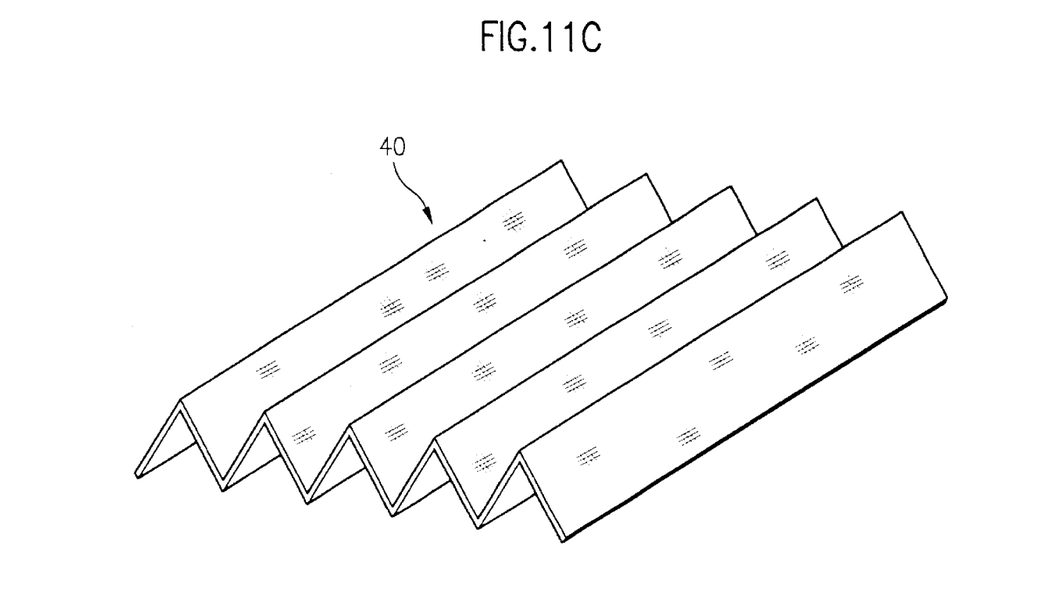

And, as shown in FIGS. 11A~11C, the photocatalyst filter may be of a plate type or preferably corrugated type with grooves each with a semicircular or triangular section for increased surface area.

In the meantime, as has been explained, the photocatalyst filter 40 of the present invention is mounted on the suction grill 20, and an energy source which can excite the photocatalyst coated on the photocatalyst filter 40 may be fitted on a position of the air conditioner 10, in fabrication of an air cleaner. However, the air filter 30 in the air conditioner is in general washed after use for a preset time, and dried under sunlight. Therefore, without fitting a separate energy source on the air conditioner for exciting the photocatalyst, if the photocatalyst filter 40 may be washed together with the air filter 30, and dried under sunlight for a preset time period, a portion of the odoring substance adsorbed onto the photocatalyst will be washed away and the other portion of the odoring substance which is not washed away is decomposed by the light. And, sterilization of harmful microbes and decomposition of the allergen are also possible. Of course, the photocatalyst filter of the present invention can be used semi-permanently.

Though this embodiment shows and explains the photocatalyst filter of the present invention applied to a window type air conditioner, the present invention is not limited to this, but application to the package type air conditioner also possible. And, of course, application of the photocatalyst filter of the present invention to other home appliances, such as a vacuum cleaner, a fan heater, and the like that require a deodoring also possible.

The photocatalyst filter, the method for fabricating the same, and the air cleaner thereof have the following advantages.

The method for fabricating a photocatalyst filter of the present invention facilitates fabrication of a photocatalyst filter, in which a photocatalyst can be coated on a base material firmly, that allows to prolong a lifetime of the photocatalyst filter without fall off of the photocatalyst from the base material. That is, as the photocatalyst does not fall off from a base material even if air is flowed by a suction force from the fan, the photocatalyst can be used in an electrostatic precipitator(air cleaner), air conditioner, fan heater, vacuum cleaner, and the like. Accordingly, when the photocatalyst filter of the present invention is used in the aforementioned air conditioner and etc., not only a deodoring performance is improved, but also sterilization of harmful microbes and decomposition of allergen are possible.

It will be apparent to those skilled in the art that various modifications and variations can be made in the photocatalyst filter, the method for fabricating the same, and the air cleaner thereof of the present invention without departing from the spirit or scope of the invention. Thus, it is intended that the present invention cover the modifications and variations of this invention provided they come within the scope of the appended claims and their equivalents.

What is claimed is:

1. A photocatalyst filter comprising:
   a base material of a predetermined shape;
   an enamel layer comprising frit and additives, wherein the enamel layer is coated on a surface of the base material, wherein the frit forms an inorganic layer on the base material, and wherein the additives form a porous surface layer on the base material; and
   a photocatalyst layer comprising a photocatalyst solution and bonding agents, wherein the photocatalyst layer is coated on the enamel layer, wherein the photocatalyst solution comprises a photocatalyst and a dispersion solvent, and wherein the bonding agents mainly comprise $SiO_2$.

2. The photocatalyst filter as claimed in claim 1, wherein the photocatalyst solution further includes zeolite or copper ion exchanged zeolite, and the photocatalyst is titanium oxide.

3. The photocatalyst filter as claimed in claim 2, wherein the photocatalyst layer further includes an antimicrobial agent.

4. The photocatalyst filter as claimed in claim 1, wherein the enamel layer comprises the frit and the additives at ratios between approximately 50:50 and approximately 80:20 wt %, wherein the frit comprises $SiO_2$ and the additives comprise $Al_2O_3$, $TiO_2$(Rutile), Li, Na, Ca or combinations thereof.

5. The photocatalyst filter as claimed in claim 4, wherein the enamel layer consists of the frit and the additives at ratio of about 65:35 to about 75:25 wt %.

6. The photocatalyst filter as claimed in claim 1, wherein the photocatalyst solution includes the photocatalyst at a mixing ratio of about 10 to about 30 wt % to the dispersion solvent.

7. The photocatalyst filter as claimed in claim 1, wherein the photocatalyst layer comprises the photocatalyst solution and the bonding agents at a ratio of about 10:90 to about 40:60 wt %.

8. The photocatalyst filter as claimed in claim 7, wherein the photocatalyst layer comprises the photocatalyst solution and the bonding agents at a ratio of about 20:80 to about 30:70 wt %.

9. A method for fabricating a photocatalyst filter, comprising:
   coating an enamel layer on a surface of a base material, wherein the enamel layer comprises frit and additives, wherein the frit forms an inorganic layer on a surface of the base material, wherein the additives form a porous surface layer on the surface of the base material; and
   coating a photocatalyst layer on the enamel layer, wherein the photocatalyst layer comprises a photocatalyst solution and bonding agents, wherein the photocatalyst solution comprises a photocatalyst and a dispersion solvent, and wherein the bonding agents mainly comprise $SiO_2$.

10. The method as claimed in claim 9, wherein the photocatlyst solution further includes zeolite or copper ion exchanged zeolite, and the photocatlyst is titanium oxide.

11. The method as claimed in claim 9, wherein the enamel layer is subjected to heat treatment at a temperature ranging from about 400 to about 600° C. for approximately one hour after the enamel layer is coated on the surface of the base material.

12. The method as claimed in claim 9, wherein the photocatalyst layer is subjected to heat treatment at a temperature ranging from about 100 to about 350° C. for approximately one hour after the photocatalyst layer is coated on the enamel layer.

13. An electrostatic precipitator, comprising:
a photocatalyst filter mounted in an air passage of the electrostatic precipitator, wherein the photocatalyst filter comprises:
a base material of a predetermined shape;
an enamel layer comprising frit and additives, wherein the enamel layer is coated on a surface of the base material, wherein the frit forms an inorganic layer, and wherein the additives form a porous surface layer; and
a photocatalyst layer comprising a photocatalyst solution and bonding agents, wherein the photocatalyst layer is coated on the enamel layer, wherein the photocatalyst solution comprises a photocatalyst and a dispersion solvent, and wherein the bonding agents mainly comprise $SiO_2$.

14. The electrostatic precipitator as claimed in claim 13, wherein the photocatalyst filter is corrugated for increasing an area of a surface thereof, and wherein the electrostatic precipitator further comprises a suction grill, an ionizer, a collector, a deodoring filter, a fan and a discharge grill.

15. A method of forming an electrostatic precipitator, comprising:
forming an air passage;
installing a photocatalyst filter in the air passage, wherein the photocatalyst filter is formed by coating an enamel layer on a surface of a base material, wherein the enamel layer comprises frit and additives, wherein the frit forms an inorganic layer on a surface of the base material, wherein the additives form a porous surface layer on the surface of the base material, and coating a photocatalyst layer on the enamel layer, wherein the photocatalyst layer comprises a photocatalyst solution and bonding agents, wherein the photocatalyst solution comprises a photocatalyst and a dispersion solvent, and wherein the bonding agents mainly comprise $SiO_2$.

16. An air conditioner, comprising:
a suction grill on an outer surface of the air conditioner;
a suction grill cover adjacent to the suction grill;
an air filter adjacent to the suction grill cover;
a photocatalyst filter adjacent to the air filter;
a heat exchanger behind the photocatalyst filter;
a fan; and
a discharge grill, wherein the photocatalyst filter comprises a base material of a predetermined shape, an enamel layer comprising frit and additives, wherein the enamel layer is coated on a surface of the base material, wherein the frit forms an inorganic layer, and wherein the additives form a porous surface layer, and a photocatalyst layer comprising a photocatalyst solution and bonding agents, wherein the photocatalyst layer is coated on the enamel layer, wherein the photocatalyst solution comprises a photocatalyst and a dispersion solvent, and wherein the bonding agents mainly comprise $SiO_2$.

17. The air conditioner as claimed in claim 16, wherein the photocatalyst filter is corrugated for increasing an area of a surface thereof.

18. The photocatalyst filter as claimed in claim 1, wherein the photocatalyst is titanium oxide, and wherein the $SiO_2$ bonding agents in the photocatalyst layer improve a coating quality and a lifetime of the titanium oxide.

19. The photocatalyst filter as claimed in claim 18, wherein the frit comprises $SiO_2$, the additives comprise $Al_2O_3$, $TiO_2$(Rutile), Li, Na, Ca or combinations thereof, and the dispersion solvent comprises isopropyl alcohol, methanol, water or a combination thereof.

20. The photocatalyst filter as claimed in claim 1, wherein the photocatalyst is a mixture of titanium oxide and zeolite.

21. The photocatalyst filter as claimed in claim 20, wherein the zeolite includes metal ions.

22. The photocatalyst filter as claimed in claim 20, wherein the zeolite comprises copper ion exchanged zeolite.

23. A photocatalyst filter comprising:
a base material of a predetermined shape;
an enamel layer comprising frit and additives, wherein the enamel layer is coated on a surface of the base material, wherein the frit forms an inorganic layer on the base material, and wherein the additives form a porous surface layer on the base material; and
a photocatalyst layer comprising a photocatalyst solution and bonding agents, wherein the photocatalyst layer is coated on the enamel layer, wherein the photocatalyst solution comprises a photocatalyst and a dispersion solvent, and wherein the bonding agents mainly comprise a non-metal bonding agent.

* * * * *